United States Patent [19]

Simpkin et al.

[11] Patent Number: 5,908,639

[45] Date of Patent: Jun. 1, 1999

[54] INHALATION POWDER CONTAINING ANTISTATIC AGENT

[75] Inventors: Gordon Thomas Simpkin; Roy Trunley; Ann-Marie Leighton, all of Dagenham, United Kingdom

[73] Assignee: Rhone-Poulenc Rorer Limited, West Malling, United Kingdom

[21] Appl. No.: 08/821,702

[22] Filed: Mar. 19, 1997

Related U.S. Application Data

[63] Continuation of application No. 08/381,930, filed as application No. PCT/GB93/01720, Aug. 13, 1993, abandoned.

[30] Foreign Application Priority Data

Aug. 14, 1992 [GB] United Kingdom .................. 9217312

[51] Int. Cl.⁶ ...................................................... A61K 9/14
[52] U.S. Cl. .......................... 424/489; 424/502; 424/490; 424/456
[58] Field of Search ..................................... 424/489, 488, 424/490; 546/318; 514/458

[56] References Cited

U.S. PATENT DOCUMENTS

| | | | |
|---|---|---|---|
| 4,916,230 | 4/1990 | Alexander | 546/318 |
| 5,039,699 | 8/1991 | Kurihara et al. | 514/458 |

FOREIGN PATENT DOCUMENTS

| | | |
|---|---|---|
| 0 160 501 | 11/1985 | European Pat. Off. . |
| 497564 | 5/1992 | European Pat. Off. . |
| 2 248 550 | 4/1992 | United Kingdom . |
| WO 88/07855 | 10/1988 | WIPO . |
| 91/16038 | 10/1991 | WIPO . |
| WO 91/16038 | 10/1991 | WIPO . |

*Primary Examiner*—Thurman K. Page
*Assistant Examiner*—William E. Benston, Jr.
*Attorney, Agent, or Firm*—Ross J. Oehler

[57] ABSTRACT

A powder composition for inhalation comprising at least one microfine drug and a carrier, in which at least a portion of the said carrier comprises an antistatic agent.

25 Claims, No Drawings

INHALATION POWDER CONTAINING
ANTISTATIC AGENT

This application is a continuation of application Ser. No. 8/381,930 filed on Apr. 24, 1995 International Application GB93/01720 filed on Aug. 13, 1993 and which designated the U.S.

This invention relates to powder compositions for inhalation and to containers suitable for use in dry powder inhalers which contain said powder compositions.

A common procedure for administering such medicaments is to inhale a unit dose of tie drug or a composition containing a unit dose of the drug by means of a specially designed inhaler. The powdered drug or composition is normally located within a container, for example a hard gelatin capsule or a blister package, or a multi-dose device so that it can be safely stored until required. The capsule or blister is ruptured or broached within the inhaler, thereby enabling the powder to be inhaled.

Generally the mean particle size of the drug used for inhalation is between 1 and 10 microns, with the size range between 2 and 5 microns being particularly suitable for treating respiratory conditions where the drug has to penetrate to the peripheral airways of the lungs. Such particle size ranges are commonly achieved by means of micronisation or spray drying. In the present specification, powders with a mean particle size within these ranges are described as "microfine", irrespective of the method by which the size of the powder is effected.

The finely divided drug powder is often administered as a composition comprising a blend or mixture of the medicament with an inert carrier. Usually the inert carrier has a mean particle size substantially larger than that of the drug. The use of a composition, as opposed to the drug alone, is advantageous because frequently the dose to be administered is very small, for example 200 micrograms or 400 micrograms. Such small quantities could not be accurately dispensed into the containers. By blending the drug uniformly with a large excess of the inert carrier, the amount dispensed into the containers is substantially increased, thus facilitating the mechanical dispensing operation.

Furthermore, the finely divided drug powders frequently exhibit very poor flow properties, which compromise the accuracy with which they can be dispensed rapidly into containers. By blending microfine drug and an excess of inert carrier which has a substantially larger median particle size, the flow properties of the composition may be enhanced and the dispensing accuracy improved.

Commonly described carrier materials include calcium carbonate and sugars, for example sucrose, mannitol or dextrose or, more particularly, lactose, which are pharmaceutically acceptable and pose no problems of toxicity, since any residues imbibed during dosing are well tolerated upon digestion or may easily be eliminated by dissolution (e.g. in the case of sugars) or mucocilliary clearance from the lung.

Machines for filling said containers are well known in the art. In this specification the part or plurality of parts of said machines which deliver the measured quantities into the containers are referred to as dosators.

In a common mechanical method of filling containers the empty containers pass to a filling position where dosators transfer powder from an adjacent bed of powder to the containers. The dosators are immersed sequentially in the powder bed to a given depth with an internal piston raised to a given position within the dosator. Each dosator then moves to the filing position, and the piston is forced down within the dosator by a cam, ejecting the powder into the containers. Subsequently the piston is returned by means of an opposed spring to its raised position and the cycle is repeated. The filled containers are then closed.

In capsule filling a machine usually first separates the two halves of the capsule shell. The bottom halves of the shells then pass to a filling position where dosators transfer powder from an adjacent bed of powder to the empty capsule portions. The dosators are immersed sequentially in the powder bed to a given depth with an internal piston raised to a given position within the dosator. Each dosator then moves to the filling position, and the piston is forced down within the dosator by a cam, ejecting the powder into the capsule. Subsequently the piston is returned by means of an opposed spring to its raised position and the cycle is repeated. The filled half-capsules are then re-capped with the other halves of the capsule shells.

Problems are often encountered through blocking or sticking of the filling equipment.

It has also been found that lactose, although otherwise entirely satisfactory as an inert diluent, often causes a particular problem during the filling process through the sticking of the dosators, which is associated with the, build-up of powder around the dosator. The adherent powder eventually becomes compacted and jams the piston from moving within the dosator.

Blocking of the powder dosators may be permanent, so that they will deliver no more powder to the empty containers until the dosators have been stripped down and cleaned, or the problem may be intermittent, so that for example the dosator may not deliver any dose from time to time, or may deliver a proportion of the required quantity of powder, or all of the required quantity of powder, in successive operations.

With high speed production equipment, particularly when low fill weights are employed, in conjunction with the use of multiple dosator delivery to the containers, the in-process control of such a process is very dependent upon the correct functioning of the dosators.

The fill weight of composition in the capsule or blister is frequently about 25 mg. This weight probably represents the maximum quantity of powder that may comfortably be inhaled without undue side effects, such as coughing, and also corresponds to the minimum quantity that is usually dispensed by filling machines.

Many inhalation drugs suffer from unpleasant side effects at high concentrations, such as tremour or nausea. Thus it is important to maximise the proportion of drug reaching the lungs, so as to reduce the likelihood of side effects caused by the proportion of drug that does not reach the lungs, but is imbibed orally.

It is a further disadvantage of existing compositions that it is difficult or impossible to deliver a substantial proportion of the dose of the medicament to the lungs.

These problems have been found to be partially or completely eliminated by previously treating all or a proportion of the inert carrier powder with an antistatic additive.

Static is the accumulation of electric charge responsible for the attractive and repulsive properties within a powder composition. Its retention can prove troublesome in processing and in final use of the composition, resulting in increased adherence of the microfine drug particles to the carrier particles, or in an increased adherence of the carrier particles to the machine dosators.

An antistatic agent in this application can be described as a substance applied to the inert carrier material, to render it less prone to becoming charged with static electricity by triboelectrification processes during processing.

Thus, according to the present invention, there is provided a powder composition for inhalation, preferably oral inhalation, comprising at least one microfine drug and a carrier, in which at least a portion of the said carrier is treated, e.g. coated, with an antistatic agent.

Suitable antistatic agents may be selected from, for example, sorbitan fatty acid esters, polyoxyethylene sorbitain fatty acid esters, dioctyl sodium sulphosuccinate, and fatty amine salts of alkylarylsulphonic acids. These additives are commonly commercially available under a variety of names, such as Span, Tween and Pentrone.

For example, sorbitan trioleate (Span 85) is a non-ionic material which has hitherto found application as an antistatic agent for textile coating processes.

The concentration of antistatic agents applied to the composition according to this invention may be from about 0.01% by weight to about 2.0%, by weight, preferably from 0.02% by weight to 1.0% by weight, more preferably from 0.1% by weight to 0.5% by weight.

Preferably, there are provided such compositions wherein the antistatic additive is pharmaceutically acceptable, more particularly, suitable for delivery to the lungs.

According to one feature of the invention there is provided a pharmaceutical composition for inhalation comprising at least one microfine drug and an inert carrier, in which all of the inert carrier is coated with the antistatic additive.

According to a further feature of the invention, there is provided a pharmaceutical composition suitable for inhalation, comprising at least one microfine drug and an inert carrier, in which a portion of the inert carrier is coated with the antistatic additive.

Preferred compositions according to the invention are those in which the carrier has a particle size distribution in which at least about 7% by weight of the carrier particles are at or below about 11 microns and at least about 20% by weight are at or below about 33 microns and at least about 20% by weight are at or above about 63 microns, more particularly those in which the carrier has a particle size distribution in which at least 8% by weight of the carrier particles are at or below 11 microns and at least 25% by weight are below 33 microns and at least. 25% by weight are above 63 microns, especially those in which the carrier has a particle size distribution in which at least 9% by weight are at or below 11 microns and at least 25% by weight are below 33 microns and at least 35% by weight are above 63 microns.

Preferred compositions according to the invention are those in which at least about 95% by weight of the antistatic agent in the said composition is coated onto carrier particles of a size greater than about 11 microns, preferably those in which at least 98% by weight of the antistatic agent in the said composition is coated onto carrier particles of a size greater than 11 microns.

Particle sizes referred to in this specification are measured by laser diffraction on a Malvern Instruments particle sizer.

Preferred compositions according to the invention are those in which the carrier is present at a concentration of from about 95.0% to 99.99%, more particularly from 97.0% to 99.9%, especially from 98.0% to 99.8%, by weight.

Processes for preparing such compositions, by the application or adaptation of known methods, also constitute features of the invention.

Thus, according to a feature of the invention, a pharmaceutically acceptable solid carrier, preferably in a fluidised bed, is sprayed with a solution of an antistatic additive in a suitable solvent, e.g. ethanol, followed by drying, preferably in a fluidised bed, followed by blending with a microfine solid pharmaceutically active compound or followed by blending with a mixture of a microfine solid pharmaceutically active compound with a finely divided pharmaceutically acceptable solid carrier.

An advantage of the pharmaceutical compositions of this invention is that, when the antistatic additive is coated preferentially onto the larger, essentially non-respirable particles of the inert carrier, it is possible to avoid or partially avoid the penetration of the antistatic agent to the peripheral airways, thereby reducing the possibility of pulmonary irritation by the antistatic agent.

As examples of medicaments which may be administered by means of the present invention there may be mentioned salbutamol sulphate, triamcinolone acetonide, calcitonins, budesonide, beclomethasone dipropionate, fenoterol, terbutaline sulphate, isoprenaline hydrochloride, and polypeptides.

As a further example of medicaments which may be administered by means of the present invention, there are provided benzamide derivatives of the general formula:

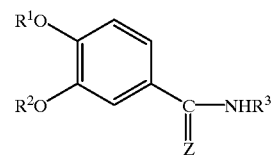

wherein $R^1$ represents a straight- or branched-chain alkyl group containing up to 4 carbon atoms, $R^2$ represents a straight- or branched-chain alkyl group containing from 2 to 15 carbon atoms or a mono-, bi-or tricycloalkyl group containing up to 10 carbon atoms, $R^3$ represents an optionally substituted phenyl, naphthyl or heterocyclyl group, preferably a 5-, 6- or 7-membered heterocyclyl group containing one or more hetero atoms selected from oxygen, sulphur and nitrogen atoms, the optional substituents being one or more substituents selected from halogen atoms, alkyl groups which may carry one or more halogen atoms, and from aryl, arylalkyl, alkoxy, aryloxy, alkylthio, arylthio, alkoxycarbonyl, aryloxycarbonyl, alkanoyl, aroyl, alkylsulphonyl, arylsulphonyl, alkylsulphinyl, arylsulphinyl, hydroxy, hydroxyalkyl, formyl, alkanoylamino, aroylamino, cyano and nitro groups, and from amino, carbamoyl and sulphamoyl groups which themselves may each carry one or two alkyl substituents, and Z represents an oxygen or sulphur atom, and when said heterocyclyl groups contain one or more nitrogen ring atoms, N-oxides thereof, and pharmaceutically acceptable salts thereof, wherein all aryl groups and moieties, unless otherwise indicated, are selected from phenyl and naphthyl groups optionally substituted by one or more substituents selected from halogen atoms and alkyl and alkoxy groups, and wherein all alkyl groups and moieties, unless otherwise indicated, are straight- or branched-chain and contain up to about 4 carbon atoms. Such benzamide derivatives, their preparation and their uses are described in the specification of Patent Cooperation Treaty Patent Application Publication Number WO 92/12961, and its equivalents filed in other countries. A particular example of such a benzamide derivative is N-(3,5-dichloropyrid-4-yl)-3-cyclopentyloxy-4-methoxybenzamide, which in the present specification for convenience is referred to as compound X.

Preferably the medicament is present in the compositions of the present invention at a concentration of from about 0.01% to about 5.0%, more particularly from 0.1% to 3.0%, especially from 0.2% to 2.0%, by weight.

In tests, the pharmaceutical compositions of this invention exhibit enhanced delivery of medicament to the second stage of a 2-stage impinger, type A, described in the British Pharmacopocia, 1988, compared to previously known compositions. This impinger is believed to be predictive of the extent of delivery to the lungs.

The following non-limitative Examples illustrate the invention.

EXAMPLE 1

The use of an antistatic agent to improve the capsule filling process was demonstrated by means of three powder compositions as shown in Table 1. Compositions A and B were according to this invention, whereas composition C was a formulation, outside the scope of this invention, for the purposes of comparison.

TABLE 1

Percentages of Constituents Employed in the Preparation of Compositions A, B and C (w/w)

| Composition | Aerosol Grade Lactose | Span 85 | Salbutamol Sulphate | Fine Grade Lactose |
|---|---|---|---|---|
| A | 78.8 | 0.4 | 1 | 19.8 |
| B | 79.0 | 0.2 | 1 | 19.8 |
| C | 79.2 | 0.0 | 1 | 19.8 |

Compositions A and B were prepared by spraying a solution of Span 85 in industrial methylated spirits onto the aerosol grade lactose, followed by drying, in a fluid bed coater/drier, to give a coated, free-flowing powder. The salbutamol sulphate and fine grade lactose were then blended with the coated lactose.

Composition C was prepared by blending the lactose and salbutamol sulphate.

The aerosol grade lactose used had a size distribution, determined by known methods by laser diffraction, of 1.7% less than or equal to 11 microns, 6.4% less than or equal to 33 microns, and 63.7% more than or equal to 63 microns, by weight, with a median size of 70.8 microns.

The fine grade lactose used had a size distribution, determined by known methods by laser diffraction, of 30% less than or equal to 11 microns, 85% less than or equal to 33 microns, and 0.2% more than or equal to 63 microns, by weight, with a median size of 18 microns.

The capsule filling performance of compositions A, B and C was then assessed using a commercial capsule filling machine (mG2). Blocking or sticking of the dosators of the machine was evidenced by an increase in the variability and a decrease in the mean weight of the contents of the capsules. The variability was measured as the relative standard deviation (RSD) of the capsule fill weight. About 3,000 capsules per hour were filled per dosator. The results are shown in Table 2.

Compared to composition C, compositions A and B gave a significant improvement in fill weight uniformity. The uniformity of capsule contents using composition C became progressively worse over a period of 0.5 to 1.5 hours and the experiment had to be abandoned. At this point the dosator showed considerable powder build-up which had become compacted and caused the pistons to jam or to be difficult to operate within the dosators.

On the other hand, compositions A and B ran consistently well over a period of 7 to 9 hours, with no signs of adverse filling characteristics. Furthermore, there was no significant build-up of the carrier around the dosators, indicating that the filling machine would have continued to function satisfactorily for a further period of time, after the end of the standard working day.

TABLE 2

Capsule Filling Performance

| Elapsed | Composition A | | Composition B | | Composition C | |
|---|---|---|---|---|---|---|
| Time (Min.) | Mean Wt. (mg) | RSD % | Mean Wt. (mg) | RSD % | Mean Wt. (mg) | RSD % |
| 0 | 24.65 | 3.30 | 25.0 | 3.18 | 23.55 | 3.51 |
| 30 | 24.10 | 3.78 | 25.25 | 2.84 | 22.32 | 13.03 |
| 60 | 24.10 | 3.78 | 24.7 | 4.17 | 20.28 | 27.05 |
| 90 | 23.15 | 3.21 | 24.7 | 2.66 | Abandoned | |
| 120 | 23.0 | 3.73 | 25.0 | 2.60 | | |
| 180 | 24.7 | 2.31 | 24.15 | 4.09 | | |
| 240 | 24.1 | 3.54 | 25.4 | 4.31 | | |
| 300 | 24.0 | 3.31 | 24.35 | 3.06 | | |
| 360 | 24.75 | 3.18 | 24.5 | 3.11 | | |
| 420 | 24.05 | 3.16 | 24.35 | 3.06 | | |
| 480 | 24.3 | 4.02 | | | | |
| 540 | 23.95 | 3.17 | | | | |

EXAMPLE 2

The use of an antistatic agent to improve the delivery of drug in vitro was demonstrated by the use of two powder compositions containing compound X.

Composition E was a dry powder formulation according to this invention, prepared by the method described for compositions A and B in Example 1, except that 0.8% w/w of compound X was substituted for the 1.0% salbutamol sulphate. Composition D was a dry powder inhalation formulation outside the scope of this invention, prepared by blending lactose and compound X, for comparison.

TABLE 3

Quantities of Constituents Used in the Preparation of Compositions D and E

| Composition | Drug (% w/w) | Span 85 (% w/w) | Aerosol grade Lactose | Fine grade Lactose |
|---|---|---|---|---|
| D | 0.8 | nil | 70 parts | 30 parts |
| E | 0.8 | 0.17 | 70 parts | 30 parts |

The delivery of compound X from compositions D and E was tested using the 2-stage impinger type A as described in the British Pharmacopoeia, 1988, at an air flow rate of 30 liters per minute, using a dry powder inhaler.

The percentage of the dose of compound X in the capsule reaching the second stage of the impinger was 25.1% for composition E., but only 20.8% for composition D.

EXAMPLE 3

The effect of modifying the particle size distribution of the carrier to improve the delivery of drug in vitro was demonstrated by the use of thee powder compositions containing compound X.

Compositions F and G fell outside the scope of this invention whereas composition H was a dry powder formulation according to this invention. The particle size data, for these compositions, determined by known methods by laser diffraction, are shown in table 4.

TABLE 4

Particle Size Distribution (percentage w/w) for the Lactose Carriers used for Compositions F, G and H

| Composition | Particle Size Distribution of Lactose Carrier | | | |
|---|---|---|---|---|
| | ≤11 μm | ≤33 μm | ≥63 μm | Median Size |
| F | 6.5% | 18.8% | 53.7% | 65 μm |
| G | 12.8% | 31.4% | 42.0% | 57.3 μm |
| H | 12.5% | 30.7% | 43.2% | 58.0 μm |

Compositions F and G were prepared by blending 0.8% by weight of compound X with lactose of the appropriate particle size distribution, whereas composition H was prepared by the method described in Example 1 for compositions A and B, except that 0.8% w/w compound X was used as the active constituent instead of the 1.0% w/w of salbutamol sulphate.

The delivery of compound X from compositions F, G and H was tested using the 2-stage impinger type A as defined in the British Pharmacopoeia, 1988, at an air flow rate of 30 liters per minute, using a dry powder inhaler. The results are shown in table 5.

TABLE 5

Percent compound X reaching stage 2 of the BP 2-stage impinger, type A

| Composition | Percent in Stage 2 |
|---|---|
| F | 12.1 |
| G | 22.1 |
| H | 27.3 |

The compositions of Example 3 demonstrated further elements of the invention. Thus composition F, which lay outside the scope of the invention, showed a relatively low proportion of drug reaching the second stage of the impinger. Composition G, although outside the scope of the invention, illustrated that by adjusting the particle size distribution of the carrier to within the range described in this invention, a significant improvement in delivery of drug to the second stage of the impinger was achieved.

Composition H, which was a composition according to the present invention, demonstrated that the use of the antistatic agent in addition to adjustment of the particle size distribution of the carrier further improved the delivery or drug to the second stage of the impinger.

We claim:

1. A powder composition for inhalation comprising at least one microfine drug and a carrier, in which at least a portion said carrier, but none of said drug, comprises an antistatic agent selected from the group consisting of a sorbitan fatty acid ester, a polyoxyethylene sorbitan fatty acid ester, dioctyl sodium sulphosuccinate and a fatty amine salt of an alkylarylsulphonic acid, where said at least one microfine drug is not a polypeptide.

2. A composition according to claim 1 in which the antistatic agent is sorbitan trioleate.

3. A composition according to claim 1 in which the antistatic agent is present at a concentration of from 0.01% by weight to 2.0% by weight.

4. A composition according to claim 3 in which the antistatic agent is present at a concentration of from 0.02% by weight to 1.0% by weight.

5. A composition according to claim 4 in which the antistatic agent is present at a concentration of from 0.1% by weight to 0.5% by weight.

6. A composition according to claim 1 in which the drug is salbutamol sulphate, triamcinolone acetonide, budesonide, beclomethasone dipropionate, fenoterol, terbutaline sulphate or isoprenaline hydrochloride.

7. A composition according to claim 1 in which the drug is a benzamide derivative of the general formula:

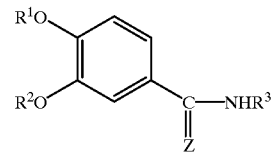

wherein $R^1$ represents a straight- or branched-chain alkyl group containing up to 4 carbon atoms, $R^2$ represents a straight- or branched-chain alkyl group containing from 2 to 15 carbon atoms or a mono-, bi- or tricycloalkyl group containing up to 10 carbon atoms, $R^3$ represents an optionally substituted phenyl, napthyl or heterocyclyl group, and Z represents an oxygen or sulphur atom, and when said heterocyclyl group contains one or more nitrogen ring atoms, an N-oxide thereof, or a pharmaceutically acceptable salt thereof.

8. A composition according to claim 7 in which the drug is N-(3,5-dichloropyrid-4-yl)-3-cyclopentyloxy-4-methoxybenzamide.

9. A composition according to claim 1 in which the drug is present at a concentration of from 0.01% by weight to 5.0% by weight.

10. A composition according to claim 9 in which the drug is present at a concentration of from 0.1% by weight to 3.0% by weight.

11. A composition according to claim 10 in which the drug is present at a concentration of from 0.2% by weight to 2.0% by weight.

12. A composition according to claim 1 in which the carrier comprises calcium carbonate or a sugar or mixtures thereof.

13. A composition according to claim 12 in which the sugar is sucrose, dextrose, lactose, or mannitol, or mixtures therefor.

14. A composition according to claim 1 in which the carrier has a particle size distribution in which at least 7% by weight of the carrier particles are at or below 11 microns and at least 20% by weight are at or below 33 microns and at least 20% by weight are at or above 63 microns.

15. A composition according to claim 16 in which the carrier has a particle size distribution in which at least 8% by weight of the carrier particles are at or below 11 microns and at least 25% by weight are below 33 microns and at least 25% by weight are above 63 microns.

16. A composition according to claim 15 in which the carrier has a particle size distribution in which at least 9% by weight are at or below 11 microns and at least 25% by weight are below 33 microns and at least 35% by weight are above 63 microns.

17. A composition according to claim 1 in which at least 95% by weight of the antistatic agent in the said composition is coated onto carrier particles of a size greater than 11 microns.

18. A composition according to claim 19 in which at least 98% by weight of the antistatic agent in the said composition is coated onto carrier particles of a size greater than 11 microns.

19. A composition according claim 1 in which the carrier is present at a concentration of from 95.0% by weight to 99.99% by weight.

20. A composition according to claim 19 in which the carrier is present at a concentration of from 97.0% by weight to 99.9% by weight.

21. A composition according to claim 20 in which the carrier is present at a concentration of from 98.0% by weight to 99.8% by weight.

22. A pharmaceutical dosage form suitable for use with a dry powder inhaler comprising a composition according to claim 1 and a container.

23. A pharmaceutical dosage form according to claim 22 wherein the container is a hard gelatin capsule.

24. A pharmaceutical dosage form according to claim 22 wherein the container is a blister package.

25. A pharmaceutical dosage form according to claim 22 wherein the container comprises a multi-dose device.

* * * * *

UNITED STATES PATENT AND TRADEMARK OFFICE
CERTIFICATE OF CORRECTION

PATENT NO.    : 5,908,639
DATED         : June 1, 1999
INVENTOR(S)   : Gordon Thomas Simpkin, et. al.

It is certified that error appears in the above-identified patent and that said Letters Patent is hereby corrected as shown below:

On the title page, item:

[63]  Continuation of application No. 08/381,930, Apr. 24, 1995, which is a 371 of PCT/GB93/01720, Aug. 13, 1993, abandoned.

Signed and Sealed this

Second Day of November, 1999

Attest:

Q. TODD DICKINSON

Attesting Officer

Acting Commissioner of Patents and Trademarks